United States Patent [19]

Stark et al.

[11] 4,164,214

[45] Aug. 14, 1979

[54] METHOD AND APPARATUS FOR MEASURING THE SENSITIVITY OF TEETH

[75] Inventors: Marvin M. Stark, Los Altos Hills; Jack B. Rosenfeld, San Francisco; Roger B. Pelzner, San Mateo; Kenneth B. Soelberg, Menlo Park, all of Calif.

[73] Assignee: The Regents of the University of California, Berkeley, Calif.

[21] Appl. No.: 818,508

[22] Filed: Jul. 25, 1977

[51] Int. Cl.² .............................................. A61B 5/05
[52] U.S. Cl. ................................... 128/741; 32/40 R
[58] Field of Search ........... 128/2 N, 2 R, 2 S, 2.1 R, 128/2.1 C, 2.1 M, 2.1 Z, 405, 406, 409, 410, 411, 419 R, 421, 422, 423; 32/40 R

[56] References Cited

U.S. PATENT DOCUMENTS

| | | | |
|---|---|---|---|
| 2,249,894 | 7/1941 | Goldenstein | 128/303.13 |
| 2,522,052 | 9/1950 | Logan | 128/2.1 R |
| 2,949,107 | 8/1960 | Ziegler | 128/2.1 R |
| 3,128,759 | 4/1964 | Bellis | 128/2.1 R |
| 3,215,139 | 11/1965 | Dietz | 128/419 R X |
| 3,295,514 | 1/1967 | Hein et al. | 128/2.1 R |
| 3,601,126 | 8/1971 | Estes | 128/303.14 |
| 3,755,900 | 9/1973 | Friedman | 128/2.1 R X |
| 3,782,366 | 1/1974 | Brown | 128/2.1 R |
| 3,782,389 | 1/1974 | Bell | 128/421 X |
| 3,830,226 | 8/1974 | Staub | 128/2.1 R |
| 3,841,311 | 10/1974 | Brown | 128/2.1 R |
| 3,943,914 | 3/1976 | Grenfell et al. | 128/2 S |
| 3,943,919 | 3/1976 | Landgraf | 128/2.1 R |
| 3,954,111 | 5/1976 | Sato | 128/419 R |

FOREIGN PATENT DOCUMENTS

| | | | |
|---|---|---|---|
| 443755 | 5/1927 | Fed. Rep. of Germany | 128/303.13 |
| 248148 | 11/1969 | U.S.S.R. | 128/2.1 R |

OTHER PUBLICATIONS

Mason et al., "Pain Sensations . . . stimulation", IEEE Transon Bio. Med. Eng., vol. 23, No. 5, pp. 405–409, Sep. 1976.

Gneco et al., "A New Apparatus for the Quantitative . . . Phys.", Med. & Bio. Eng., vol. 9, No. 6, pp. 705–710, 1971.

Primary Examiner—Lee S. Cohen
Attorney, Agent, or Firm—Flehr, Hohbach, Test, Albritton & Herbert

[57] ABSTRACT

A dental apparatus for measuring the sensitivity of teeth. The apparatus includes an electrode probe for contacting a tooth and an electrical lead for forming a complete circuit with the probe through the tooth. Electrical energy is applied to the tooth in varying amounts; the apparatus measures and records the quantitative magnitude of a parameter proportional to the effective electrical energy applied to the tooth.

11 Claims, 2 Drawing Figures

METHOD AND APPARATUS FOR MEASURING THE SENSITIVITY OF TEETH

BACKGROUND OF THE INVENTION

1. Field of the Invention

This invention generally relates to dental appliances and, more particularly, to devices for measuring the sensitivity of teeth.

2. Description of the Prior Art

One of the most controversial testing methods in dentistry today is electric pulp testing. Many researchers have concluded that the validity of such pulp tests is debatable and that little or no correlation can be found between the pain-perception threshold and the histologic status of the pulp. In contrast, the American Dental Association Council for Materials and Devices stated in 1973 that electric pulp testers are a valid aid to dental diagnosis when handled and used correctly.

This controversy stems first from the subjective variability in human oral structure. For example, the enamel and dentin morphology, the surface conditions of the tooth, and the complex oral environment all can cause false and sometimes negative data. In addition, the mental and emotional state of the patient as well as the administration of drugs can influence the patient's response.

The second factor causing this controversy stems from the electrical and mechanical shortcomings of the electrical pulp testers that are commercially available today. Most of these pulp testers form an electrical circuit through the dentist and rely on the contact between the dentist's free hand and the patient. Such a circuit is subject to substantial variation in circuit resistence. Further, some researchers have found that there is no correlation between the dial settings and the output of some present pulp testers. None of the commercially available instruments today make quantitative measurements of the electrical energy applied to the tooth. The present day instruments all make relative measurements which cannot be correlated with other pulp testers. In addition, the relative measurements of these instruments have great operator induced variability and, thus, have little scientific value. Another problem with the prior art has been that the onset of pain was the threshold reference; but in fact the onset of pain is a condition of overstimulation.

OBJECT AND SUMMARY OF THE INVENTION

It is an object of the present invention to provide a novel method and apparatus that overcomes the limitations and disadvantages of the prior art.

A further object of the present invention is to objectively detect the different states of pulpal vitality by measuring a parameter having biological significance. This parameter is proportional to the quantitative magnitude of the effective electrical energy that induces a threshold response from the dental pulp being tested.

An additional object of the present invention is to yield accurate, reproducible, and reliable data. The present invention eliminates subjective variables and provides high-resolution results.

Another object of the present invention is to provide a system that can be easily used by one person and automatically provide a permanent printed record of the data measured.

A still further object of the present invention is to provide data that is capable of meaningful analysis. The high-resolution, reliability, and reproducibility of the data facilitates collection of numerous results and permits statistically significant deductions. This feature is especially important for clinical research on tooth desensitising compounds and topical anaesthetics.

In addition, the present invention is capable of accurately measuring dental pulp sensitivity with any electronic pulp tester in use today. The present invention measures a parameter proportional to the amount of effective energy applied to the tooth and is therefore independent of the shape of output wave form or its frequency. Although there is some general agreement that a mid-range frequency AC current should be used for pulp testing, there is no standardized wave form and each company manufactures instruments having different output wave forms.

These and other objects and advantages are achieved by a method and apparatus which includes an electrode probe for electrically contacting a tooth and an electrical lead for contacting the patient's oral tissue. The lead and the probe form an electrical circuit with the tooth and the quantitative magnitude of a proportional parameter to the effective electrical energy applied to the tooth is measured. The apparatus also includes means for recording this measurement.

Additional objects and features of the invention will appear from the following description in which the preferred embodiment has been set forth in detail in conjunction with the accompanying drawings.

DESCRIPTION OF THE PREFERRED EMBODIMENT

The preferred embodiment uses a method of diagnosis based upon the threshold response from dental pulp to measured amounts of electrical stimuli. The irritability of the nerve fibers in the dental pulp is dependent upon and varies with the metabolism of the pulp. The pulp, in turn, is influenced by pathological changes in the tissues. In general, pulp threshold measurements are sufficiently accurate to diagnose both sensitivity (hyperemia) and non-vitality (necrosis).

Figure 1:
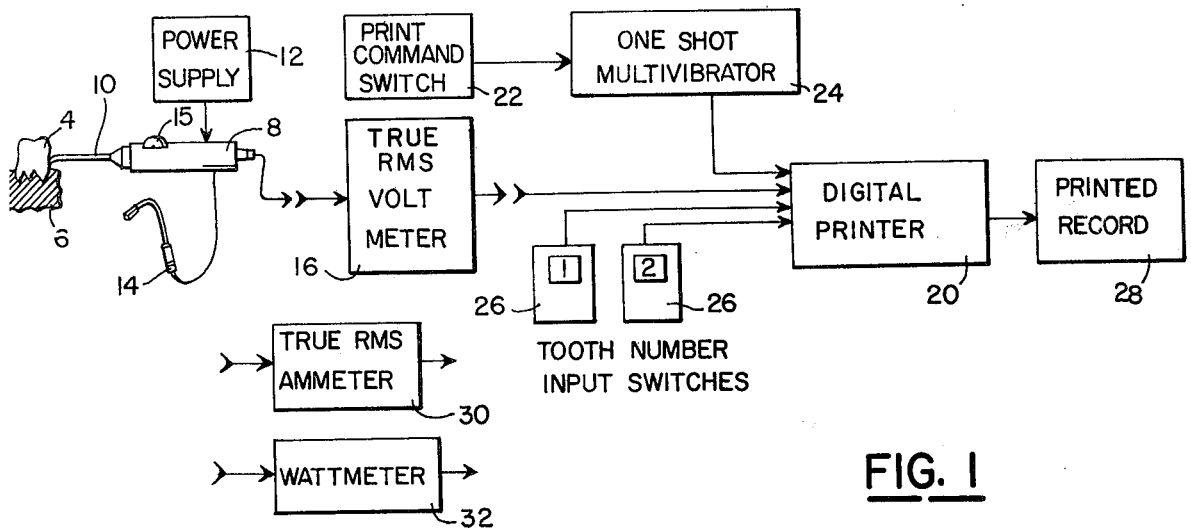
FIG. 1 is a block diagram of an apparatus for measuring the sensitivity of teeth according to the present invention.
Figure 2:
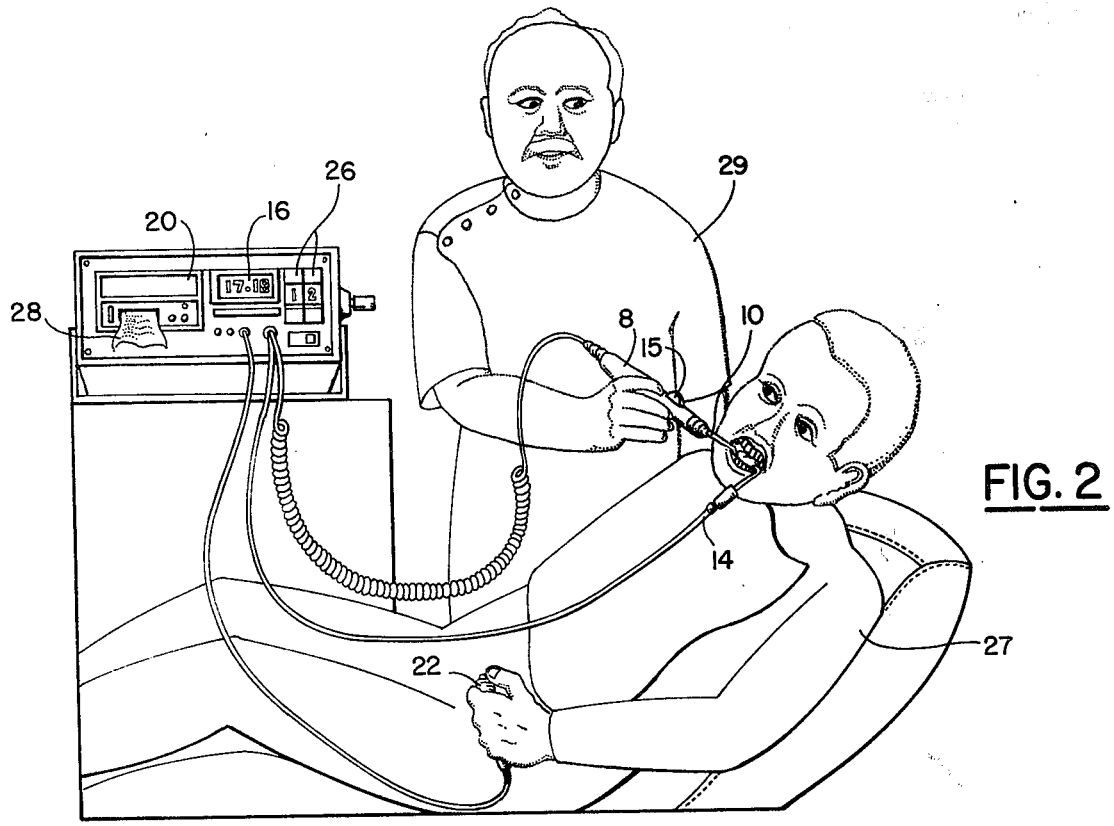
FIG. 2 is a diagrammatic view of the apparatus of FIG. 1 illustrating its operation.

Referring to FIGS. 1 and 2, the apparatus includes an electronic pulp tester that forms a circuit which applies electrical energy through a tooth 4 and its associated gum tissue 6. The pulp tester includes a probe 8 to which is attached an electrode tip 10. The electrode tip is tapered and forms the focus of electrical contact with the tooth 4. The probe is energized by a DC power supply 12. The power supply can either be an internal battery or an external regulated DC power supply operated from 120 volt household current. The output of the electronic pulp tester is a non-sinusoidal wave form having a frequency of about 400 Hz. The magnitude of the output can vary between 0 and 45 volts true RMS.

The electrical circuit through the tooth 4, FIG. 1, and the gum tissue 6 is completed by a ground lead 14 that is operatively connected to the probe.

The ground lead includes a question-mark shaped brass tube connected to the probe 8 by an electrical lead. The brass tube is shaped so as to hang inside the mouth of the person 27 whose teeth are being measured and to electrically contact the oral tissue of the patient via the electrically conductive saliva in the buccal reflex area of the mouth.

The output of the pulp tester is controlled by a finger-actuated rotary rheostat 15. The rheostat dial is detented to assure small and controlled increases or decreases of electrical output from the probe in step-by-step non-linear increments. The dial of the rheostat is also numbered so that anyone can return to one of the predetermined output levels to verify a measurement and the condition of the tooth being tested. The use of a detented rheostat dial permits any operator 29 to apply predetermined levels of electrical energy to the tooth and thereby guarantee reproducibility. In the preferred embodiment the rheostat is constructed to vary the output level step-by-step in a logarithmic manner. The output is varied in sufficiently, closely controlled incremental steps to eliminate the possibility of over-stimulation and consequent pain to the patient being tested. A tingling sensation and/or a feeling of warmth is now the experienced threshold reference, and as such elicits excellent patient acceptance.

In one embodiment actually constructed, a Digilog electronic pulp tester was modified to operate with the apparatus disclosed herein. This pulp tester is available from the Demetron Research Corporation of Ridgefield, Connecticut 06877.

The amount of electrical energy applied to the tooth 4 is measured by a meter 16. This meter measures the proportional parameter of the effective electrical energy applied to the tooth. The measurement of effective electrical energy corresponds to the net biological stimulus received by the tooth from the electricity. Typically, the value of the effective electrical energy is proportional to the root-mean-squared (RMS) value of either the output current or voltage. More specifically, the RMS or effective value of an AC voltage corresponds to a DC voltage of the same magnitude passing through a pure resistor. Likewise, the RMS or effective value of an AC current corresponds to the same magnitude of direct current passing through a pure resistor.

A true RMS meter 16, FIG. 1, is also used in order to permit the apparatus to adapt to any of the commercially available electronic pulp testers. At the present time there are many pulp testers available on the market, and each has a different, non-sinusoidal output. Although there is some agreement among dental researchers that dental pulp stimulation requires mid-range frequency AC voltages, no one has established the optimum wave form for a stimulating signal. Thus, each manufacturer uses a different output wave form. By employing a true RMS meter, a parameter proportional to the effective electrical energy applied to the tooth can be measured. A true RMS measurement is virtually independent of the frequency and shape of the output wave form, and is therefore independent of the probe used.

In the preferred embodiment a temperature compensated, digital volt meter 16 measuring true RMS voltage is used. The meter has an operating range of from 0 to 60 volts AC. The meter also has an update rate of at least 10 times per second in order to remove any significant time lag between the actual output of the probe 8 at the moment of sensation and the meter reading. The output of the meter 16 is also visually displayed to the operator 29. This display permits the operator to monitor the increase in voltage and the progress of each measurement.

The apparatus also includes a digital printer 20 that prints out on a paper tape 28 numerical information corresponding to the binary-coded decimal input to the printer. The printer receives the measurement from the meter 16 on four channels in binary-coded decimal. The digital printer 20 is actuated by a print command switch 22 which is connected to a one-shot multivibrator 24. The print command switch is a finger-actuated switch held by the person whose tooth is being measured. The one-shot multivibrator 24 insures that only one print command signal is sent to the digital printer and eliminates multiple printouts when the command switch to the printer is held down.

The digital printer 20 also receives two binary-coded decimal numbers from the two tooth number input switches 26. These switches are touch-activated, thumb-wheel type switches on which the operator 29 can select the number of the tooth being tested. When the print command switch 22 is actuated, the digital printer records on a permanent record 28 the true RMS voltage reading of the output of the probe 8 and the number of the tooth selected on the input switches 26.

The operation of the apparatus is illustrated in FIG. 2. Typically, the patient 27 is comfortably seated in a dental chair and the tests are performed by an operator 29. The patient holds the print command switch 22 in one hand and the apparatus with its visual display is prominently located in front of the operator.

Electrical pulp testing is a method of diagnosis based upon the response of dental pulp to electrical stimuli. The operator 29 gradually increases the electrical energy applied to the tooth until the threshold level of initial electrical sensation is felt by the patient 27. To perform the measurement, the operator first dries the tooth being measured and removes any foreign matter from the surface of the tooth that may cause a short circuit. Next, the operator places a conductive gel on the tooth so that a good electrical contact can be made between the electrode tip 10 and the tooth 4. The operator then places the ground lead 14 in the patient's mouth so that the question-mark shaped end is in electrical contact with the patient's oral tissue. The electrode tip is next placed in contact with the tooth at a position generally away from the gun and in the middle of the cervical one-third of the tooth.

To begin the measurement, the operator 29 commences to increase the electrical energy applied to the tooth. The electrical circuit comprises the electrode 10, the tooth 4, the gum 6, and the ground lead 14. The probe 8 is designed so that the output increases logarithmically and the rheostat 15 is of detented construction so that the variation occur step-by-step. The operator increases the output until the patient 27 first senses either a tingling sensation or a feeling of warmth in the tooth being tested. When this occurs, the patient actuates the print command switch 22 that causes the printer 20 to record on the paper tape 28 the data on its input terminals. The printer records the true RMS voltage measured by the meter 16 across the output of the probe and the number of the tooth selected by the operator 29 on the tooth number input switches 26. The printer prints these values on a paper tape that forms a permanent record of the measurements.

The above operation is repeated over and over for each tooth in the patient's mouth. The result is a printed record 28 listing all of the teeth by number and the threshold sensitivity to stimulation of each tooth as recorded by the patient 27.

The present invention also contemplates the use of a true RMS ammeter 30 or wattmeter 32 in the apparatus described above. The RMS ammeter measures the quantitative amount of effective current passed through the tooth 4 and sensed by the patient 27. A measurement of true RMS current is made both to determine the biological magnitude of the current and also to make the measurement virtually independent of the output wave form of the probe. The wattmeter 32 records the value of the average electrical power passed through the tooth 4. The average power is the product of the RMS current and the RMS voltage. In other words, the wattmeter measures the product of the effective values of these two parameters.

By measuring either the true RMS voltage, the true RMS current, or the average electrical power the apparatus measures either the effective electrical energy applied to the tooth or a proportional parameter thereof.

Although the preferred embodiment is disclosed with a logarithmic rheostat, the output of the pulp tester can be controlled with any device that regulates the output in closely controlled, small, incremental steps.

The present invention has application in a wide variety of uses. In particular, this apparatus can be used for testing the effect of topically applied proprietary tooth de-sensitising compounds. In addition, this apparatus can be used to test the intensity and duration of topical anaesthetics. The apparatus can also be used as a diagnostic tool for an endodontist and also to provide a printed record of the base line value for all teeth at the commencement of a procedure. The printed tape 28 provides a permanent record that can be used for both diagnostic purposes and scientific investigations.

Thus, although the best modes contemplated for carrying out the present invention have been herein shown and described, it will be apparent that modification and variation may be made without departing from what is regarded to be the subject matter of the invention.

What is claimed is:
1. Apparatus for measuring the sensitivity of teeth in oral tissue, comprising:
   (a) an electrode probe adapted for electronically contacting a tooth;
   (b) a power supply connected to the electrode probe for applying electrical energy to said probe;
   (c) an electrical lead connected to the power supply and adapted for making electrical contact with negligible contact resistance with oral tissue around the tooth being measured;
   (d) means within the probe for varying the rate of electrical energy passing through the tooth from the probe; and
   (e) means connected to the varying means for measuring the rate of effective electrical energy delivered to the tooth by the probe.

2. An apparatus as in claim 1 in which the electrical measuring means is a wattmeter which measures the rate of electrical energy passing through the tooth.

3. Apparatus for measuring the sensitivity of teeth in oral tissue, comprising:
   (a) an electrode probe adapted for electrically contacting a tooth;
   (b) a power supply connected to the electrical probe for delivering electrical energy to said probe;
   (c) an electrical lead connected to the power supply and adapted for completing an electrical circuit with the probe and the tooth and for making electrical contact with negligible contact resistance with the oral tissue around the tooth thereby delivering electrical energy to the tooth;
   (d) means within the probe for varying the rate of electrical energy delivered by the circuit to the tooth;
   (e) means connected to the varying means for measuring the quantitative magnitude of a parameter proportional to the rate of effective electrical energy delivered by the circuit to the tooth;
   (f) printing means connected to the measuring means for recording on a permanent medium the magnitude of said energy parameter; and
   (g) means connected to the printing means for commanding the printing means to record the magnitude of said energy parameter, said printer commanding means being adapted for actuation by the person whose tooth sensitivity is being measured.

4. An apparatus as in claim 3 in which the electrical measuring means is a true RMS voltmeter measuring $V_{RMS}$ when $$V_{RMS} = \sqrt{\frac{1}{T} \int_0^T [v(t)]^2 \, dt},$$

where v(t)=the instantaneous voltage as a function of time and T=the period of the voltage wave.

5. An apparatus as in claim 3 in which the electrical measuring means is a true RMS ammeter measuring $I_{RMS}$ where $$I_{RMS} = \sqrt{\frac{1}{T} \int_0^T [i(t)]^2 \, dt},$$

where i(t)=the instantaneous current as a function of time and T=the period of the current wave.

6. An apparatus as in claim 3 including means connected to the printing means for recording on a permanent medium a symbol identifying the tooth being measured together with the quantitative magnitude of said energy parameter.

7. An apparatus as in claim 3 in which the electrical energy varying means is a detented logarithmic rheostat that varies in small step-by-step increments the amount of electrical energy delivered by the circuit to the tooth and thus provides the person moving the rheostat with tactile feedback of the change in electrical energy.

8. An apparatus as in claim 3 including means connected to the printing means for visually displaying both the magnitude of said energy parameter and a symbol identifying the tooth being measured.

9. Apparatus for measuring the sensitivity of teeth in oral tissue, comprising:
   (a) an electrode probe adapted for electrically contacting a tooth;
   (b) a power supply connected to the probe for delivering electrical energy to said electrode probe;
   (c) an electrical lead connected to the power supply and adapted for making electrical contact with negligible contact resistance with the oral tissue around the tooth;

(d) means connected to the probe for varying the true RMS voltage applied to the tooth by the probe; and
(e) means connected to the varying means for measuring the true RMS voltage applied to the tooth by the probe where:

$$V_{RMS} = \sqrt{\frac{1}{T} \int_o^T [v(t)]^2 \, dt,}$$

where v(t)=the instantaneous voltage as a function of time and T=the period of the voltage wave form.

10. A method for measuring the sensitivity of teeth, comprising the steps of:
(a) electrically stimulating a tooth by applying electrical energy thereto by using an electrode probe;
(b) measuring the quantitative magnitude of a parameter proportional to the rate of effective electrical energy delivered to the tooth by the probe; and
(c) printing on command on a permanent medium the quantitative magnitude of said energy parameter, said printing being commanded by the person whose tooth sensitivity is being measured.

11. A method as in claim 10 in which the step of printing also includes printing on the permanent medium a symbol identifying the tooth being measured.

* * * * *